(12) United States Patent
Rothrum et al.

(10) Patent No.: US 6,187,126 B1
(45) Date of Patent: Feb. 13, 2001

(54) METHOD FOR MAKING A REFASTENABLE TUBE AND CABLE RESTRAINT (75) Inventors: Robert J. Rothrum, Coon Rapids; Robert L. Wheeler, Woodbury; F. Andrew Ubel, St. Paul, all of MN (US)

(73) Assignee: 3M Innovative Properties Company, St. Paul, MN (US)

( * ) Notice: Under 35 U.S.C. 154(b), the term of this patent shall be extended for 0 days.

(21) Appl. No.: 09/000,690

(22) Filed: Dec. 30, 1997

Related U.S. Application Data (62) Division of application No. 08/209,424, filed on Mar. 10, 1994, now Pat. No. 5,707,703.

(51) Int. Cl.$^7$ ............................ A61M 5/32; B29C 53/02
(52) U.S. Cl. .................. 156/200; 156/204; 156/217; 156/227; 156/289; 604/178; 604/179; 604/180
(58) Field of Search ...................... 156/66, 289, 324, 156/249, 269, 199, 200, 204, 217, 227; 604/179, 180, 174, 175, 176, 177, 178; 128/DIG. 26

(56) References Cited

U.S. PATENT DOCUMENTS

| | | |
|---|---|---|
| Re. 24,906 | 12/1960 | Ulrich .......................... 206/59 |
| D. 256,162 | 7/1980 | Haerr et al. ................. D24/52 |
| 2,292,272 | 8/1942 | Hirshfield ...................... 40/2 |
| 2,387,593 | 10/1945 | Lesser ........................ 117/68.5 |
| 2,902,734 | 9/1959 | Walters ........................... 24/7 |
| 3,430,300 | 3/1969 | Doan ............................ 24/73 |
| 3,677,250 | 7/1972 | Thomas ....................... 128/348 |
| 3,826,254 | 7/1974 | Mellor ........................ 128/133 |
| 3,865,770 | 2/1975 | Blake ......................... 260/27 R |
| 4,027,665 | 6/1977 | Scrivens .................... 128/132 D |
| 4,057,066 | 11/1977 | Taylor ....................... 128/349 R |
| 4,074,397 | 2/1978 | Rosin ......................... 27/73 AS |
| 4,097,627 | 6/1978 | Nemeth et al. ................. 428/40 |
| 4,122,857 | 10/1978 | Haerr ......................... 128/348 |
| 4,134,398 | 1/1979 | Scrivens .................... 128/132 D |
| 4,314,415 | * 2/1982 | De Woskin ...................... 40/21 |
| 4,324,237 | 4/1982 | Buttaravoli ................. 128/214 R |
| 4,413,080 | 11/1983 | Blake ........................... 524/187 |
| 4,447,238 | 5/1984 | Eldridge, Jr. .................. 604/280 |
| 4,457,754 | 7/1984 | Buttaravoli ................... 604/180 |

(List continued on next page.)

FOREIGN PATENT DOCUMENTS

| | | |
|---|---|---|
| 1038716 | 9/1978 | (CA) . |
| 88 11 126 U | 5/1989 | (DE) . |
| 0 206 558 | 12/1986 | (EP) . |
| 2 235 629 | 3/1991 | (GB) . |
| 2 251 796 | 7/1992 | (GB) . |
| 2 253 350 | 9/1992 | (GB) . |
| WO 93/22996 | 11/1993 | (WO) . |
| WO 94/26223 | 11/1994 | (WO) . |

OTHER PUBLICATIONS

TNT Moborg International Ltd. product literature.

*Primary Examiner*—Michael W. Ball
*Assistant Examiner*—Gladys Piazza
(74) *Attorney, Agent, or Firm*—Yen Tong Florczak (57) ABSTRACT

The present invention provides a tube and cable restraint comprising: a strip of flexible material having a generally elongated rectangular loop-section adapted to form a loop about the tube with an attachment means near the first end of the loop-section adapted to secure (e.g., adhere) the strip to a surgical drape and a refastenable loop forming means adapted to secure (e.g., adhere) the second end of the loop-section to the first end thereby forming a loop around the tube or cable. In another embodiment, the restraint is adapted to secure a tubular drape around a projecting object such as a microscope eyepiece.

2 Claims, 6 Drawing Sheets

U.S. PATENT DOCUMENTS

| | | | |
|---|---|---|---|
| 4,522,853 | 6/1985 | Szonn et al. | 428/40 |
| 4,534,762 | 8/1985 | Heyer | 604/180 |
| 4,569,960 | 2/1986 | Blake | 524/145 |
| 4,614,183 | 9/1986 | McCracken et al. | 128/132 R |
| 4,669,458 | 6/1987 | Abraham et al. | 128/133 |
| 4,678,462 | 7/1987 | Vaillancourt | 604/180 |
| 4,770,913 | 9/1988 | Yamamoto | 428/41.9 |
| 5,010,899 | 4/1991 | Thompson | 128/849 |
| 5,019,071 | 5/1991 | Bany et al. | 604/389 |
| 5,037,397 | 8/1991 | Kalt et al. | 604/174 |
| 5,038,778 | 8/1991 | Lott | 128/207.17 |
| 5,076,289 | 12/1991 | Darling | 128/877 |
| 5,098,399 | 3/1992 | Tollini | 604/180 |
| 5,100,393 | 3/1992 | Johnson | 604/180 |
| 5,125,907 | 6/1992 | Philpott | 604/80 |
| 5,125,995 | 6/1992 | D'Haese et al. | 156/155 |
| 5,147,322 * | 9/1992 | Bowen et al. | 604/180 |
| 5,158,557 | 10/1992 | Noreen et al. | 604/389 |
| 5,160,315 * | 11/1992 | Heinecke et al. | 602/180 |
| 5,266,401 | 11/1993 | Tollini | 428/343 |
| 5,270,111 | 12/1993 | D'Haese et al. | 428/356 |
| 5,304,146 | 4/1994 | Johnson et al. | 604/180 |
| 5,593,750 | 1/1997 | Rothrum et al. | 428/40.1 |

* cited by examiner

METHOD FOR MAKING A REFASTENABLE TUBE AND CABLE RESTRAINT

This is a division of application Ser. No. 08/209,424 filed Mar. 10, 1994, now U.S. Pat. No. 5,707,703.

FIELD OF THE INVENTION

This invention relates to tube and cable restraints used to temporarily fasten tubes and cables to a patient's body or to a surgical drape and to restraints used to temporarily secure a drape around an object such as a microscope eyepiece. This invention also relates to surgical drapes having such restraints attached thereto.

BACKGROUND OF THE INVENTION

There is a great need to economically fasten or restrain elongated tubes or cables (hereinafter sometimes generically referred to as "tubes") to a patient's body or to a surgical drape. For example, restraints are needed which can fasten feeding tubes or other cables to a patient, fasten irrigation and drainage tubes to a patient or to the patient's bed, or fasten other tubes and/or cables to a surgical drape, thus keeping the tubes and/or cables in an organized fashion and out of the way of the surgical field.

Depending on the type of tube or cable it is sometimes desirable that the tube or cable be easily adjusted through the restraint. By "adjusted" or "adjustable," is meant that the tube or cable should be able to slip through the restraint in response to a desired force. This allows the tube or cable to be adjusted easily should an additional length of tube or cable be needed on either side of the restraint. In other situations the adjustment of the tube or cable should be restricted and the tube or cable not allowed to easily slip through the restraint.

It is also desirable that the tube or cable be easily removed or released from the restraint without need to cut the tube or cable. Preferably, the tube or cable should be easily removed or released from the restraint without the restraint being damaged. More preferably, the tube or cable restraint should be refastenable. By "refastenable," is meant that the tube or cable restraint should allow multiple securings and releasings of the tubes and/or cables. This is in contrast to those restraints which only function to secure a cable once (i.e., the release of the cable causes destruction of the securing means or the cable integrity). In addition, preferred tube or cable restraints should be easily used with only one hand. This would allow the user to grasp one or more tubes and cables in one hand and still operate the restraint with the other hand. Most preferably, the tube or cable restraint should be easily used when the user's hands are gloved.

Unfortunately, prior attempts to produce such a versatile tube and cable restraint have failed to achieve these requirements. The restraints are either too expensive, not adjustable, not refastenable, or lack ease of use and versatility. It would be desirable to produce a tube and cable restraint that is economical, refastenable, and versatile.

U.S. Pat. No. 3,430,300 (Doan) discloses a fastener for medical tubes comprising a cloth strip provided with a layer of pressure sensitive adhesive for securing the strip in place and a "T" shaped adhesive end portion which is wrapped around a tube, folded and overlapped around the facing part of the strip, thereby holding the loop fast. Unfortunately, the fastener lacks ease of use due to the need to fold the adhesive coated wings of the "T" shaped end around the strip. It is believed that this folding operation would be very difficult to perform with one hand, especially when the hand is gloved. In addition, this fastener lacks refastenability. There is no convenient way to unfasten the folded, adhered "T" shaped end portion to allow multiple securings and releasings of the tubes and/or cables.

U.S. Pat. No. 3,677,250 (Thomas) discloses a tabbed anchoring tape comprising at least one anchoring tab portion with an adhesive coated strap for wrapped engagement with a tube. Notably, the strap comprises an adhesive coating along one side. Unfortunately, this anchoring tape is not readily refastenable and lacks ease of use and versatility. To engage the tubing the adhesive tape is wrapped completely around the tube (thus potentially contaminating the tube with adhesive residue) and the free end of the tape adhered to an inner portion of the tape. There is no convenient way to unfold the adhesive tape to allow multiple securings and releasings of the tubes and/or cables.

U.S. Pat. No. 4,027,665 (Scrivens) discloses a surgical drape which includes a retainer means for securing thin flexible elements such as suction tubing and electrical wires to the upper surface of the drape. The retainer means comprises a long loop of the drape material. The loop runs along the edge of the drape and along the entire length of the panel. In use, the tube or wire is threaded through the long loop. This retainer means lacks easy access. To remove a tube or wire from the loop the tube or wire must be pulled through the full length of the loop. In addition, tubes or wires with bulky ends cannot be easily threaded through this retainer.

U.S. Pat. No. 5,100,393 (Johnson) discloses a tube holder comprising a flat base for application to the body and a material riveted or snapped to the base with a connection means. Several different connection means are disclosed including irreversible fasteners, adhesive tapes, or hook and loop structures.

RELATED APPLICATIONS

Of related interest are U.S. Pat. Nos. 5,616,385 and 5,593,750 and U.S. patent application Ser. No. 08/208,990, which are herein incorporated by reference.

SUMMARY OF THE INVENTION

The present invention provides inexpensive tube and cable restraints which are both adjustable and refastenable. The restraints may be easily operated with only one hand. In general, the tube and cable restraints comprise an elongated strip of flexible material having a first means for attachment to a surface and a second means for repositionably forming a loop from said strip. In a presently preferred embodiment the strip is plastic and has an adhesive material near one end to attach the strip to a surface such as a surgical drape and a second adhesive material positioned to repositionably connect the two ends of the strip together and form a loop around a cable or tube. Preferably, the strip has an elongated loop-section that is free of adhesive and a finger tab adapted to facilitate easy opening and closing of the loop.

In an alternative embodiment of the present invention a restraint suitable for securing a drape around a microscope eyepiece is provided. In general, this restraint comprises an elongated strip of flexible material having a first means for attachment to the drape and a second means for repositionably forming a band from said strip. In a presently preferred embodiment the strip is plastic and has an adhesive material on one end to attach the strip to the surgical drape and a second adhesive material positioned to repositionably connect the two ends of the strip together and form a band around the object.

BRIEF DESCRIPTION OF THE DRAWINGS

FIG. 1c illustrates the restraint in use.

FIGS. 2a and 2d illustrate alternative attachment means.

DETAILED DESCRIPTION OF THE INVENTION

The tube restraints of the present invention comprise an elongated strip of flexible material having a first means for attachment to a surface and a second means for repositionably forming a loop from said strip. In a presently preferred embodiment the strip has an adhesive material near one end (e.g., to attach the strip to a surface such as a surgical drape or a patient's skin) and a second adhesive material positioned to repositionably connect the two ends of the strip together and form a loop around a cable or tube. Preferably, the strip has an elongated loop-section that is free of adhesive and adapted to be folded around a tube or cable.

In an alternative embodiment of the present invention a restraint suitable for securing a drape around an elongated member (e.g., cylindrical or duct shaped object such as a microscope eyepiece) is provided comprising an elongated strip of flexible material having a first means for attachment to the drape and a second means for repositionably forming a band from said strip. In a presently preferred embodiment the strip has an adhesive material on one end (e.g., to attach the strip to the surgical drape) and a second adhesive material positioned to repositionably connect the two ends of the strip together and form a band around the object, thereby securing the drape to the object. Preferably, the strip has an elongated band-section (analogous to the loop-section of the previous embodiment) that is free of adhesive and adapted to be wrapped around the object.

The elongated loop-section should be sufficiently strong, for a given width, to support the forces which may be imparted upon it from the cable. Preferably, the loop-section material should be sufficiently strong to support the gravitational weight of the cable, more preferably, the material should be sufficiently strong to resist moderate "tugging forces" which may be imparted to the loop when the surrounded cable is pulled or jerked. Most preferably, the loop-section material has a sufficient strength to resist tearing or breaking prior to the adhesive failure of the attachment means, the breaking of the cable being secured, or the cohesive failure of the surface being attached to (such as a tearing of the drape material). Suitable loop-section materials have a tensile strength of at least 4 N/cm width when tested according to ASTM D882 as herein modified. Preferred loop-section materials have a tensile strength of at least 5 N/cm width, more preferably at least 10 N/cm width, most preferably at least 13 N/cm width. If desired, the loop-section material may comprise a layer of a toughening material (e.g., a layer of glass fibers oriented in the lengthwise direction or a layer of another high strength sheet material) to strengthen the flexible loop-section material of the restraint.

The loop-section material should be flexible enough to easily fold back on itself and form a loop. Materials which easily break or tear when so folded are considered to be unsuitable for use in this invention. The loop-section's flexibility should be maintained over the entire operating range of the restraint. Materials which lose their flexibility at temperatures between 0° C. and 100° C. should preferably be avoided.

Suitable loop-section materials for use in the present invention include sheet materials or laminates comprising cloth, nonwoven fabrics, foams or plastic materials. Presently preferred loop-section materials include plastic sheet materials. Suitable plastic sheet materials include naturally based organic polymers such as acetate, azlon, rayon, and triacetate; and synthetically prepared organic polymers such as acrylic, aramid, nylon, olefin (e.g., poly(1-butene), polycarbonate, polyethylene, polyester, poly(3-methyl-1-butene), poly(1-pentene), polypropylene, and polystyrene), polysulfone, polytetrafluoroethylene, poly(vinyl alcohol), poly(vinyl chloride), poly(vinylidine chloride), and poly(vinylidine fluoride). Preferred synthetic polymers include; acetate, acrylic, nylon, polypropylene, polyethylene, polyester, and rayon. Most preferred synthetic polymers include polyethylene films. Preferred materials are nontoxic, more preferably hypoallergenic, and are most preferably also environmentally safe (e.g., may be recycled or disposed of in a manner which does not harm the ecosystem).

As previously mentioned, the flexible loop-section material may comprise an elastomeric material. Suitable elastomeric materials include natural rubber, polyisoprene, polybutadiene, diene styrene copolymers, ethylene propylene copolymers, ethylene propylene diene terpolymers, styrene butadiene block copolymers, styrene isoprene block copolymers, and polyurethanes such as spandex.

If desired, the loop-section material may comprise a laminate of more than one material. For example, a first material may be bonded, coated or secured to a different second material. The first material may provide the laminate with the necessary compatibility with the attachment means (e.g., a pressure sensitive adhesive as discussed below) while the second material may provide the laminate with the necessary physical integrity or strength.

The loop-section material should be compatible with the desired attachment means and with the desired refastenable loop forming means. Several different attachment means are discussed in more detail below. The loop-section material should be selected so as to function with the selected attachment means. For example, when the selected attachment means comprises a sonic weld the loop-section material must withstand and be compatible with sonic welding. Likewise, when the selected attachment means comprises an adhesive tape the surface of the loop-section material must be capable of being adhered to.

When formed into a loop the loop-section material surrounds the tube or cable. Depending on the type of tube or cable it is sometimes desirable that the tube or cable be easily adjusted through the restraint. By "adjusted," is meant that the tube or cable should be able to slip through the restraint in response to a desired tension force. This allows the tube or cable to be adjusted easily, even without opening the loop, should an additional length of tube or cable be needed on either side of the restraint. In other situations the adjustment of the tube or cable should be restricted and the tube or cable not allowed to easily slip through the restraint. The ability of a given tube or cable to slip through a loop of a particular loop-section material depends on the friction between the loop-section material and the tube or cable and the amount of "slack" around the cable (i.e., the length of loop material in excess of the minimum length needed to wrap around the cable). The amount of slack can be adjusted by the user by variably positioning the loop forming means along the adjustment area. In addition, proper selection of loop-section material (or for a laminate the proper selection of the layer of material in contact with the tube or cable) can provide the desired level of friction between the tube and the loop. For example, a common tube used to connect a urinary catheter to a collection bag is made from poly(vinyl chloride). To prevent slip of this tube through the loop one would preferably select a material having a high friction coefficient with poly(vinyl chloride) such as polyethylene. In contrast, a common cable used in an operatory suite is an electrical cable covered in poly(vinyl chloride). To allow easy repositionability through a loop one would select a material having a low friction coefficient with poly(vinyl chloride) such as teflon.

For use as a tube and cable restraint the loop-section should be long enough to wrap around the tube(s) or cable(s) being secured. In a preferred embodiment an elongated strip of flexible material is used to form the loop-section as well as provide areas for the placement of the attachment means and the loop forming means. For example, the loop forming means preferably comprises an adhesive material which connects two portions of the elongated flexible strip thereby forming a loop. Thus, the flexible material should be long enough to provide: a suitably sized loop around the desired tube(s) or cable(s); a suitable region for placement of the attachment means; a suitable region for the placement of the loop forming means; and, preferably, a suitably sized finger tab. Preferred tube and cable restraints for use in the medical field comprise a loop-section of at least 5 cm, more preferably at least 8 cm, and most preferably at least 10 cm. To accommodate the attachment means, loop forming means, and finger tab, preferred tube and cable restraints comprise an elongated strip of flexible material of at least 9 cm, more preferably at least 12 cm, and most preferably at least 14 cm. Longer restraints may be utilized if desired.

The width of the restraint will depend on several factors. For example, the minimum strength requirements to function as a restraint may determine a minimum width and/or thickness for a particular material. In addition, the minimum required surface area of the attachment means and/or loop forming means may dictate a minimum width of the restraint. Furthermore, it is contemplated that the width required for the loop-section may not be the same as the width required for the attachment means or loop forming means. For example, a wider attachment means and loop forming means may be utilized with a narrower loop-section material. However, for reasons of economy, it is presently preferred to fabricate the restraints of the present invention from a generally rectangular piece of flexible material. Thus, the width of the loop- section, the attachment means, and the loop forming means are preferably similar. Preferred tube and cable restraints for use in the medical field have a width of at least 1 cm, more preferably at least 2 cm, and most preferably between 2 and 5 cm.

The thickness of the loop-section of the present invention should be sufficient to provide the loop with enough strength yet not so thick that the loop-section resists deformation into a loop around the tube or cable being secured. The minimum thickness will generally depend on the width of the loop-section material (in general, the strength of a material depends on the material's "cross section"). Suitable films used to form typical restraints of the present invention have a thickness of at least 0.02 mm, more preferably a thickness of at least 0.04 mm, and most preferably a thickness between 0.07 and 0.2 mm.

Alternatively, the loop-section material may comprise a non-sheet material such as a rope or tube. The rope or tube may be attached to a suitable attachment means and loop forming means (e.g., comprising a suitable adhesive tape component as herein described) to construct a suitable restraint. The length of a suitable non-sheet loop-section material is desirably the same as for a sheet material. In addition, the cross section of the rope or tube material is desirable similar to suitable sheet materials used for the loop-section. Finally, if desired, an elongated strip of flexible material, having a suitable attachment means, a suitable loop forming means, and optionally a suitable finger tab may be "drawn" to neck down the loop-section or may be die cut in a manner to narrow the loop-section.

In the alternative embodiment, the band-section material should be strong enough and flexible enough to secure the fabric around an elongated member. It is expected that the band-section will not encounter the tugging forces of the tube and cable restraint embodiment. Thus weaker materials may be employed if desired. Suitable band-section materials include those materials which are suitable for the loop-section materials. Materials which are somewhat elastomeric are preferred for securing fabrics around solid elongated members as these materials easily form closely fitting snug bands around the solid objects. The close fit helps secure the material to the object. As previously noted, the material should be compatible with the desired attachment means and band forming means. The length, width, and thickness of the band-section material should be adjusted depending on the size of the object being secured and the other previously noted factors.

The restraints of the present invention may be pre-attached to an article (such as a surgical drape or gown) or may be provided as individual restraints which are attached to a surgical drape or gown at the time of use. In addition, the restraints of the present invention may be provided as individual tube and cable restraints which are attached to a patient's skin at the time of use. Depending on the intended use the attachment means may be varied as described herein. In general, a wider variety of attachment means are contemplated for use with article surfaces than with skin.

For use with pre-attached restraints on an article the attachment means may comprise a suitable mechanical attachment means or an adhesive attachment means. Suitable mechanical attachment means include, for example, metallic or plastic staples, snaps, or rivets, or sewing with thread. In addition, the restraints of the present invention can be tied to the article, integral with the article (e.g., formed from the fabric of the drape or gown), or sonically welded thereto. Suitable adhesive attachment means include, for example, thermoplastic or thermosetting adhesives, pressure sensitive adhesives ("PSA") or tapes comprising the same. Preferred adhesive attachment means include the pressure sensitive adhesives or PSA tapes discussed herein. Preferably, the attachment means is "permanent," i.e., the restraint, once attached to the drape or gown, is not relocatable on the drape or gown and is permanently attached to that position. For use with individual "point-of-use" restraints (i.e., restraints which are individually provided for attachment to a drape, gown or a patient's skin at the time of use) the attachment means is preferably an adhesive attachment means. The adhesive attachment means is preferably secured near one end of the elongated strip of flexible material, more preferably attached to the surface of the elongated strip of flexible material. The adhesive attachment means may comprise one or more adhesive layers and optionally one or more backing layers. To protect the adhesive attachment means from surface contamination, the adhesive surface is preferably covered (e.g., with a separate liner material) prior to use. If desired, the adhesive surface may be covered prior to use with another portion of the elongated strip instead of a separate liner material.

Suitable pressure sensitive adhesives for use in the present invention include those pressure sensitive adhesives which are capable of providing the necessary amount of peel strength and/or shear strength to function in the manner required (e.g., sufficient strength when used as the attachment means to securely attach the restraint to the surface without unintended detachment). Suitable adhesives for use in the medical field should be non-toxic, preferably hypoallergenic, and are most preferably also environmentally safe.

Suitable pressure sensitive acrylate adhesives for use in the present invention include copolymers which are reaction products of the polymerization of at least one "A" monomer and at least one "B" monomer to yield a copolymer having an inherent viscosity of about 1.0 dl/g to about 2.0 dl/g. The A monomer is a polymerizable monomer comprising an acrylate or methacrylate ester of a non-tertiary alcohol or a mixture of non-tertiary alcohols with the alcohols having from 1 to 14 carbon atoms and desirably averaging about 4 to 12 carbon atoms. The B monomer is an ethylenically unsaturated compound and desirably may be acrylic acid, methacrylic acid, itaconic acid, acrylamide, methacrylamide, acrylonitrile, methacrylonitrile, vinyl acetate, N-vinyl pyrrolidone, or combinations thereof. The A monomer is polymerizable and contributes the viscoelastic properties of the pressure sensitive adhesive copolymer. Non-limiting examples of such A monomers include the esters of acrylic acid or methacrylic acid with non-tertiary alkyl alcohol such as 1-butanol, 1-pentanol, 2-pentanol, 3-pentanol, 2-methyl-1-butanol, 1-methyl-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2 -octanol, 1-decanol, 1-dodecanol, and the like. Such monomeric acrylic or methacrylic esters are known in the art, and many are commercially available.

The B monomer is an ethylenically unsaturated compound copolymerized with the A monomer to affect the physical properties of the resulting pressure sensitive adhesive copolymer. In general, the presence of the B monomer will reduce the flexibility of the resulting pressure sensitive adhesive copolymer. Thus, the weight percentages of the A monomer and the B monomer should be balanced in order to provide a pressure sensitive adhesive copolymer having an inherent viscosity of from about 1.0 dl/g to about 2.0 dl/g. The weight percentage ratio of A monomer: B monomer ranges from about 85:15 to about 98:2 and desirably from about 90:10 to 97:3.

The pressure sensitive adhesive copolymer should be tacky at room temperature as well as at skin temperature of mammals. Also, the adhesive should be hypoallergenic, i.e., after continuous contact with skin, there is no significant skin sensitization or irritation during adhesion. Often, to determine if an adhesive is hypoallergenic, the following evaluations are conducted: cell cytotoxicity, skin irritation, and sensitization potential. The United States Food and Drug Administration recommends such evaluations in a Tripartite Biocompatibility Draft Guidance for Medical Devices. The commercially available medical tapes described herein using acrylate pressure sensitive adhesives of the type described herein are generally considered hypoallergenic. Presently preferred as an acrylate pressure sensitive adhesive for tapes used in the present invention is an isooctyl acrylate/acrylic acid copolymer in a weight ratio of about 94:6. The inherent viscosity of the copolymer is about 1.4–1.6 dl/g. Preferably, acrylate pressure sensitive adhesives have a tackifier added to the formulation to improve tack. Commercially available tackifiers include "Foral" branded colophony acid rosins, such as "Foral AX" and "Foral 85" rosins, commercially available from Hercules Corporation, and partially hydrogenated methylstyrene hydrocarbon resins, such as "Piccolastic A25" resin, also commercially available from Hercules Corporation. Such tackifiers can be added during preparation of the acrylate pressure sensitive adhesive in an amount of about 35–40 weight percent of the copolymer solids.

Alternate pressure sensitive adhesives useful in the present invention are hypoallergenic Kraton rubber-based pressure sensitive adhesives produced using styrene-butadiene or styrene-isoprene copolymers commercially available as Kraton branded copolymers from Shell Oil Company of Houston, Texas. A variety of Kraton based pressure sensitive adhesives are disclosed in U.S. Pat. Nos. 5,019,071 (Bany et al.) and U.S. Pat. No. 5,158,557 (Noreen et al.), the disclosures of which are incorporated by reference herein. Preferred as Kraton rubber-based pressure sensitive adhesives are Kraton 1107, Kraton 1111, Kraton 1101, and Kraton D branded copolymers, tackified with compatible tackifiers such as Escorez™ 1310LC branded tackifier commercially available from Exxon Chemicals, a solid $C_5$ tackifying resin commercially available as Wing-tack™ Plus brand tackifier from Goodyear Tire and Rubber Company, Akron, Ohio and naphthenic oils having 10% aromatics commercially available as Shellflex™ 371 from Shell Oil Company. Such tackifiers can comprise about 45 to about 70 weight percent of the pressure sensitive adhesive, while the Kraton copolymer can comprise about 30 to 55 weight percent. Presently preferred is a Kraton based pressure sensitive adhesive comprising about 35 weight percent Kraton 1111, about 53 weight percent Wingtack Plus, about 11 weight percent Shellflex 371, and about 2 weight percent Irganox 1010 and 1076 branded antioxidants, in a similar formulation to that disclosed in Examples 1–13 of U.S. Pat. No. 5,019,071.

Additional alternate pressure sensitive adhesives useful in the present invention are the water-dispersible pressure sensitive adhesives disclosed in U.S. Pat. Nos. 3,865,770; 4,413,080; 4,569,960; 5,125,995; and 5,270,111 and in U.S. patent application Ser. Nos. 07/763,823; 07/889,647; and 08/093,080 the disclosures of which are herein incorporated by reference.

Pressure sensitive adhesive copolymers can be copolymerized using known polymerization techniques such as emulsion polymerization and solution polymerization. Sources of polymerization preparation and techniques include *Organic Polymer Chemistry,* Saunders et al. (Halsted Publishing Company, New York 1973); *Applied Polymer Science,* Tess et al. (American Chemical Society, Washington, D.C., 1981); *Principles of Polymerization,* Odien (John Wiley and Sons, New York, 1981); and the *Handbook of Pressure-Sensitive Adhesive Technology, Second Edition,* Satas, Ed., (Van Nostrand Reinhold Company, New York, 1989), the disclosures of which are incorporated by reference. Specifically, acrylate pressure sensitive adhesive copolymers can be prepared according to U.S. Pat. No. 2,884,126/RE 24,906 (Ulrich), the disclosure of which is incorporated by reference herein. The presently preferred acrylate copolymer pressure sensitive adhesive can be prepared by emulsion polymerization according to Example 5 of U.S. Pat. No. 2,884,126/RE 24,906, except that tackifier is added to the emulsion in an amount of about 35–40% weight percent of copolymer solids, and that tackified copolymer is dissolved in a heptane-isopropanol (70:30) solution. The presently preferred Kraton copolymer pressure sensitive adhesive can be prepared in the manner as disclosed in Examples 1–13 of U.S. Pat. No. 5,019,071, the disclosure of which is incorporated by reference above.

In one embodiment, the attachment means comprises a "single-sided" adhesive tape (i.e., a tape comprising a backing and a PSA coated on one side of said backing) which is partially affixed to one end of the elongated strip of flexible material. This leaves a portion of the single-sided adhesive tape free for attachment to the surface. The free portion of adhesive tape is preferably protected, prior to use, with a liner material. The liner material may be easily peeled away from the tape to expose the adhesive. Suitable single-sided adhesive tapes are discussed below.

In another embodiment, the attachment means comprises a "double-sided" adhesive tape (i.e., a tape comprising a backing and a PSA coated on both sides of said backing) one side of which is affixed near one end of the elongated strip of flexible material. This leaves a second exposed adhesive side available for attachment to the surface. The exposed adhesive is preferably covered prior to use with a liner material. Suitable double-sided adhesive tapes are discussed below.

If desired, a suitable pressure sensitive adhesive may be directly coated on the flexible material (e.g., at one end of the strip) and covered with a liner. This avoids the necessity of the "backing" material of a single-sided or double-sided tape. The choice whether to directly coat an adhesive on the restraint or to utilize a pre-coated adhesive tape is not believed to be critical to the operation of the invention. Rather, it is presently believed that this choice will merely impact the unit cost of the restraints. However, the assembly of pre-coated tapes to a flexible material is believed to be somewhat simpler and less prone to quality problems than the direct coating of an adhesive on the flexible material.

The restraints of the present invention further comprise a refastenable loop forming means or a refastenable band forming means. The refastenable loop forming means converts the essentially planar elongated loop-section into a loop capable of securing a cable or tube. Similarly, the refastenable band forming means converts the essentially planar elongated band-section into a band capable of securing a drape around an elongated member (such as a microscope eyepiece, human wrist, etc.).

Suitable refastenable loop forming means connect the opposing ends of the loop-section material thereby forming a loop. The refastenable loop forming means of the present invention preferably employs a pressure sensitive adhesive tape which, when fastened, provides sufficient shear strength to minimize unintended loop opening yet provides peel adhesion which can be a minimum sufficient to permit facile reopening of the loop with minimal manual dexterity required. The refastenable loop forming means may be positioned near either end or both ends of the elongated strip of flexible material. Preferably, the refastenable loop forming means is pre-attached to one of the ends of the elongated strip.

It is desirable that the tube or cable be easily removed or released from the restraint without need to cut the tube or cable. Preferably, the tube or cable should be easily removed or released from the restraint without the restraint being damaged, i.e., the restraint should be refastenable. By "refastenable," is meant that the tube or cable restraint should easily allow multiple securings and releasings of the tubes and/or cables, even with a gloved hand. This is in contrast to those restraints which only function to secure a cable once (i.e., the release of the cable causes destruction of either the securing means or the cable). Similarly, for use as a drape restraint, the band should be easily opened and adjusted to allow the drape to be secured around the object.

Preferred refastenable loop forming (or band forming) means comprise an adhesive material. More preferably, the loop forming (or band forming) means comprises a pressure sensitive adhesive. Suitable pressure sensitive adhesives include the pressure sensitive adhesives discussed above in connection with the attachment means. The pressure sensitive adhesive may be provided as a coating on the elongated strip of flexible material or as part of a double-sided or single-sided tape as herein described.

In one embodiment the refastenable loop forming (or band forming) means comprises a double-sided adhesive tape which is secured to one end of the elongated strip of flexible material. The double-sided adhesive tape may be secured to the elongated strip of flexible material near either end of the restraint (i.e., near the attachment means or at the opposite end of the flexible material). The first side of the double-sided adhesive tape is used to secure, preferably permanently secure, the loop forming means to the elongated strip. The exposed second side of the double-sided adhesive tape is used to connect, preferably refastenably connect, the opposing ends of the loop-section material thereby forming a loop. Preferably, the exposed second side of the double-sided adhesive tape is covered prior to use with a release liner. This preserves the tack of the exposed adhesive of the second side, If desired, the restraint can be manufactured in the form of a loop and without a separate liner material. In essence, the adjustment area of the elongated strip functions as a liner, protecting the tack of the second side.

In order to help prevent transfer of the double-sided tape from one end of the restraint to the other, the loop forming means preferably is constructed in such a manner that the first side of the adhesive tape adheres more tenaciously to the elongated strip than the second side adheres to the adjustment area. This may be accomplished in a number of ways. For example, in one system the loop forming means comprises a tape component comprising a field of a first pressure sensitive adhesive coated on a first surface of a first backing and a field of a second pressure sensitive adhesive coated on a second and opposite surface of the first backing. Preferably, the first pressure sensitive adhesive field has a higher tack based on larger unit area and optionally a heavier coating weight than the second pressure sensitive adhesive field. "Higher tack" refers to the surface adhesiveness due to amount of surface coverage and optionally coating weight notwithstanding the fact that the two fields have the same or similar adhesive formulation. Thus, there is a differential adhesiveness ratio based on amount of surface exposed. For ease of manufacturing and use, the pressure sensitive adhesive of the first field preferably has the same or substantially similar adhesive properties as the pressure sensitive adhesive of the second field. "Same or substantially similar adhesive properties" means the formulations chosen for adhesives are not substantially distinguishable in adhesive properties but need not be the same formulation. Further, the second pressure sensitive adhesive field occupies less than the entire surface of the tape component on which the second pressure sensitive adhesive field is coated during an intended use. Tapes having this structure are more fully described in Co-pending U.S. patent application Ser. No. 08/058,439, filed on May 7, 1993 by the assignees of the present invention, which is herein incorporated by reference. Alternatively, one may coat a less aggressive pressure sensitive adhesive (or a lower coating weight of a PSA) on the second surface compared to the first adhesive coated on the first surface. Both methods will facilitate release of the tape from the adjustment area before the first side of the tape would release from the elongated strip. The peel and shear strength of the loop forming means generally increases as the surface area of the second side increases. The total surface area of the least aggressive side should be sufficient to provide the necessary shear strength to minimize unintended loop opening during use.

In another embodiment the refastenable loop forming (or band forming) means comprises a single-sided adhesive tape which is secured to one end of the elongated strip and covering at least one aperture through the elongated strip. In a similar manner to the previous embodiment, the single-sided adhesive tape may be secured to the elongated strip at either end of the restraint (i.e., near the attachment means or at the opposite end of the loop-section material). The single-sided tape is secured to the restraint by contacting the elongated strip between or around the apertures. This leaves a portion of adhesive "exposed" wherever an aperture exists. This exposed adhesive will be used to connect, preferably refastenably connect, the opposing ends of the loop- section material thereby forming a loop. Preferably, the exposed adhesive is covered prior to use with a release liner. This preserves the tack of the exposed adhesive. If desired, a separate liner may be provided for each exposed portion of adhesive. The liner(s) may be removed as additional adhesion is needed. Alternatively, the restraint can be manufactured in the form of a loop and without a separate liner material. In essence, the adjustment area of the loop-section material functions as a liner, protecting the tack of the exposed adhesive. The number of apertures and the shape of the apertures can be adjusted to provide more or less exposed adhesive, and more or less adhesive tack. For example, the apertures can be in the shape of circles, triangles, rectangles or other polygon shapes. To provide support for the single-sided tape it is preferred that the total surface area of the apertures not exceed about 90% of the surface area of the single-sided tape. More preferably, the total surface area of the apertures should not exceed about 70% of the surface area of the single-sided tape. Most preferably the total surface area of the apertures should be between about 30 and 50% of the surface area of the single-sided tape. As the surface area of the apertures increases the peel strength and shear strength of the loop forming means generally increases. The total surface area of the apertures should be sufficient to provide the necessary shear strength to minimize unintended loop opening during use.

Suitable tape components for use in the present invention (for either the attachment means, the loop forming means, or the band forming means) include commercially available medical tapes. As previously mentioned, depending on the construction of the article suitable tapes include either double-sided tapes (i.e., tapes coated with adhesive on two major surfaces) or single-sided tapes (i.e., tapes coated with adhesive on one major surface).

Non-limiting examples of acceptable double-sided tape components include No. 1509 transparent polyethylene 0.124 mm double-coated medical tape; No. 1512 transparent polyethylene 0.086 mm double-coated medical tape; No. 1513 transparent polyester 0.086 mm double-coated medical tape; No. 1522 transparent polyethylene 0.160 mm double-coated medical tape; No. 9874 transparent polyethylene 0.122 mm double-coated medical tape; No. 9920 0.024 mm double-coated polyethylene restraint tape; No. 9877 0.114 mm double-coated polyester high performance tape; and No. 9878 water dispersible adhesive tape 0.1 mm double-coated medical tape. All of the above-identified commercially available tapes, (except No. 9877 tape which is a Kraton based medical tape), consist of an appropriate backing coated on both sides with a hypoallergenic, pressure sensitive acrylate adhesive wound with a silicone treated bleached Kraft-Glassine paper liner for adhesive protection. All of the above-identified commercially available tapes are available from Minnesota Mining and Manufacturing Company of St. Paul, Minn., U.S.A. Most of these medical tapes are identified in 3M *Medical Specialties Product Reference Guide* published by 3M Health Care in 1991 and available from 3M Medical Specialties Department, the disclosure of which is incorporated by reference herein. The remainder of these medical tapes are also available in publications from 3M Medical Specialties Department. Alternatively, other commercially available tapes are useful. One example is No. 9416 tape commercially available from Minnesota Mining and Manufacturing Company. It is a double coated tape of two different pressure sensitive adhesives having different coating masses flood coated on opposing surfaces of a backing.

Suitable commercially available single-sided medical tapes for use in the present invention include, for example, No. 1523 tan 0.13 mm polyethylene medical tape; No. 1526 transparent 0.13 mm polyethylene medical tape; No. 9830 transparent 0.07 mm polyethylene medical tape; and No.

9835 white 0.14 mm coextruded ethylene vinyl acetate/ polyethylene medical tape. Nos. 1523, 1526, and 9830 medical tapes have matte finishes on the non-adhesive surface. Nos. 1523 and 1526 medical tapes have matte finished, non-adhesive surfaces which are corona treated. All of the tapes are coated on one surface with a hypoallergenic, pressure sensitive acrylate adhesive. All of the tapes are wound with a bleached Kraft paper liner (optionally slit lengthwise) having a silicone-treated, polyethylene coated surface. The liner (or a portion of the liner) may be separated from the tape during application of the tape to the restraint and, if desired, reapplied to the exposed portion of adhesive (e.g., the adhesive which is not covered by the strip due to the apertures). All of these enumerated medical tapes are commercially available from Minnesota Mining and Manufacturing Company.

Additional suitable commercially available single-sided medical tapes for use in the present invention include, for example, tapes having nonwoven backings such as No. 1505 heat-sealable 0.16 mm medical tape; No. 1529 microporous rayon nonwoven 0.14 mm medical tape; No. 1776 spunlaced polyester nonwoven 0.29 mm medical tape; No. 9903 microporous nylon nonwoven 0.23 mm medical tape; and No. 9906-W white elastic polyurethane nonwoven 0.23 mm medical tape. All of these enumerated medical tapes are commercially available from Minnesota Mining and Manufacturing Company.

Figure 5:
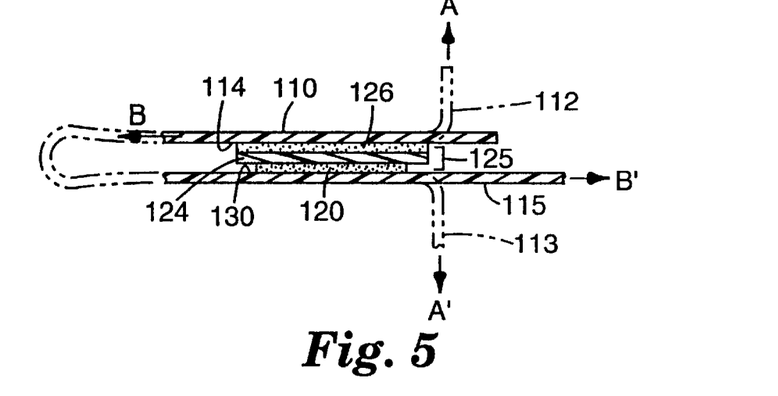
FIG. 5 is an enlarged cross section of the loop forming means of a tube and cable restraint of the present invention illustrating the "T-peel" peel force testing mode and the dynamic shear force testing mode.

Peel force in a "T-Peel" direction is used to determine the ease by which the loop forming means of the present invention can be opened by an axial peeling of one end 112 from the other end 113 (as shown in FIG. 5). A "T-Peel" peel force and strength is generated and measured by gripping the ends in an appropriate tensile testing machine (e.g., an INSTRON model 1122 operating at a displacement rate of 30.5 cm/min.) and applying an increasing force as depicted by arrows "A" and "A'." Peel force is measured in Newtons/centimeter width (N/cm). Initial peel force of the tape component 125 from the adjustment area 130 can range from about 0.09 N/cm to about 2.80 N/cm, desirably from about 0.35 N/cm to about 1.45 N/cm, and preferably from about 0.70 N/cm to about 1.00 N/cm. Such peel force minimizes dexterity required for intended opening of the loop.

Dynamic shear force is used to measure the strength of the loop forming means to resist unintended opening of the loop by shear forces applied to the loop forming means at an angle other than the axis of the restraint. A dynamic shear force and strength is generated and measured by gripping ends 114 and 115 in an appropriate tensile testing machine (e.g., an INSTRON model 1122 operating at a displacement rate of 30.5 cm/min.) and applying an increasing force as depicted by arrows "B" and "B'." Dynamic shear force is measured in Newtons/centimeter$^2$ (N/cm$^2$). Dynamic shear strength of the loop forming means can range from about 5 N/cm$^2$ to about 90 N/cm$^2$, desirably from about 10 N/cm$^2$ to about 20 N/cm$^2$, and preferably from about 12 N/cm$^2$ to about 17 N/cm$^2$ in order to assure closure of the loop.

It is preferred that the peel force of adhesive 126 from the elongated strip 110 is greater than the peel force of fastening adhesive 120 from the adjustment area 130. It is also presently preferred that the loop forming means has at least as high a dynamic shear strength as the tensile strength of the elongated strip to which the loop forming means is adhered.

Preferably, when the tube or cable restraint of the present invention is attached to and lying flat against a surface (e.g., a surgical drape), the exposed adhesive surface of the loop forming means lies away from the surface. For example, when the restraint is attached to a surgical drape and is laying flat on the drape, a tube or cable may then be laid across the restraint and the restraint folded across the tube. The exposed surface of adhesive is preferably facing up prior to the restraint being folded over the tube. This position allows easy folding of the restraint and connection of the two ends of the restraint, thereby forming a loop. In contrast, for restraints used to secure a drape to a duct shaped object (e.g., a microscope eyepiece) the exposed adhesive surface of the band forming means is preferably positioned in a manner which allows the band forming means to become "sandwiched" between the two adjacent overlapping layers of band material as the band is wound around the object.

A feature of the restraints of the present invention is the refastenable loop forming means and the refastenable band forming means. The restraints of the present invention preferably allow multiple securings and releasings of the tubes, cables, or objects. This is beneficial in situations where the user desires to add or remove cables from the restraint, or adjust the position of the cable or tube. Most preferably, the tube or cable restraint should be easily used with only one gloved hand. This allows the user to grasp the tubes or cables in one hand yet still operate the restraint. Most preferably, the restraint comprises a finger tab to facilitate easy opening and closing of the loop forming or band forming means. The finger tab should be of a sufficient size to be easily grasped between the gloved finger and thumb of a typical user, without the glove sticking to the restraint. Preferably, the finger tab is at least 100 mm$^2$, more preferably, the finger tab is at least 400 mm$^2$, most preferably, the finger tab is at least 600 mm$^2$. For ease of manufacture the finger tab may comprise a free length of the elongated strip of flexible material that either extends past the loop forming means when the loop is formed or past the band forming means when the band is formed. For example, if the loop forming means lies next to the attachment means the finger tab merely comprises an extra length of the elongated strip of flexible material (i.e., material past the adjustment area). Alternatively, if the loop forming means lies on the opposite end of the restraint from the attachment means then the finger tab may comprise an extra section of material extending past the loop forming means. If desired, one may fabricate the finger tab from a separate component and attach the finger tab to the restraint.

Preferably, the entire restraint should be capable of being sterilized. Several different sterilization processes are used in the medical field. For example, steam autoclave, gamma radiation, and ethylene oxide may be employed. Preferred restraints should withstand at least one cycle through the desired sterilization process. For example, preferably the restraint should remain functional after irradiation with up to at least 25 kGys gamma cobalt-60 radiation, a dosage often used for sterilization of medical devices.

Figure 6A:
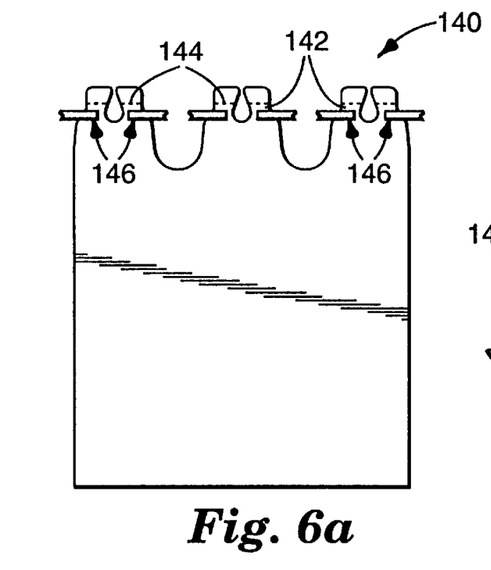
FIGS. 6a, 6b, and 6c illustrate a restraint of the present invention used to secure a drape about a microscope eyepiece and a drape comprising a plurality of restraints attached thereto.
Figure 6B:
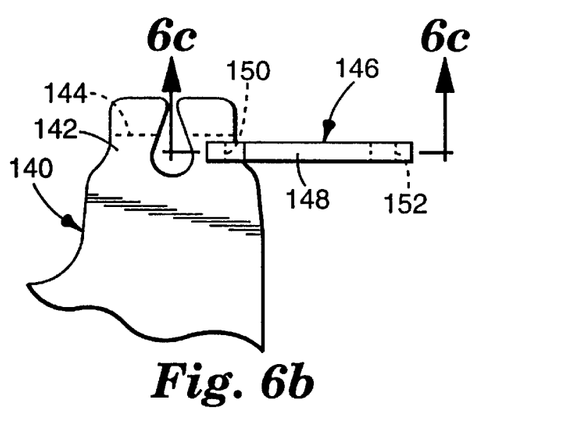
Figure 6C:
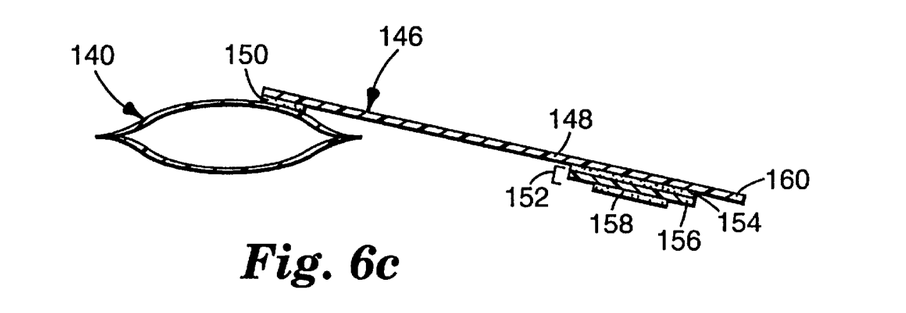

As previously mentioned, the refastenable restraints of the present invention can be used to secure a drape material to an object such as a microscope eyepiece. This embodiment is illustrated in more detail in FIG. 6. In addition to this use it is anticipated that this embodiment may be used to secure a material around a limb (e.g., to closely secure the loose fabric of a trouser to a leg or to closely secure the loose fabric of a surgical gown around a wrist). The refastenable band has many advantages over simple tape wrappings. For example, prior to use the adhesive band forming means can be easily covered (e.g., with a liner). In use, the non-adhesive portions of the band would allow adjustment of the gathered fabric while the adhesive portion would allow formation of virtually any size band. When combined with an elastomeric band-section material the restraint would allow variable tension to be applied to the object. For example, a tourniquet can be readily formed from the restraint (e.g., a restraint can attached to a patient's gown and utilized to restrict the flow of blood down a limb).

To facilitate the use of a restraint (or help the user determine whether a restraint has been properly used), the restraint may further comprise a visual indicator (e.g., a color indication means). For example, tube and cable restraints of the present invention may comprise multi-colored materials. The use of color may assist the user in a variety of ways. In one embodiment, the "adjustment area" of the tube and cable restraint may be colored in a manner such that when the loop forming means is engaged the colors blend or add together. This helps indicate whether (or to what extent) the loop forming means is in fact engaged. For example, the adjustment area may comprise a cyan colored film while the adhesive loop forming means may be colored yellow. When the yellow adhesive is contacted against the cyan film a new green color is observed. The size of the green region indicates the effective size of the loop forming means. This indication helps avoid unintentional "misses" between the loop forming means and the adjustment area. In addition, the finger tab of a restraint may be colored in a distinctive manner (or printed with a distinctive pattern) to direct the users attention to that region.

DETAILED DESCRIPTION OF THE DRAWINGS

Figure 1A:
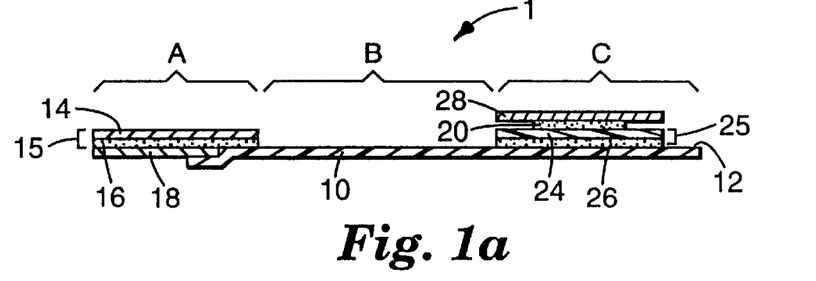
FIG. 1a is a cross section of a tube and cable restraint of the present invention having an attachment means for securing the restraint to a surface and a refastenable loop forming means for holding a tube or cable.
Figure 1B:
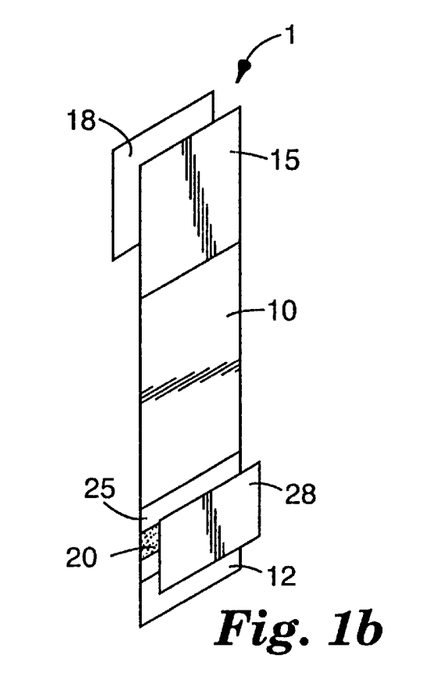
FIGS. 1b and 1c are perspective schematic views of the same tube and cable restraint where
Figure 1C:
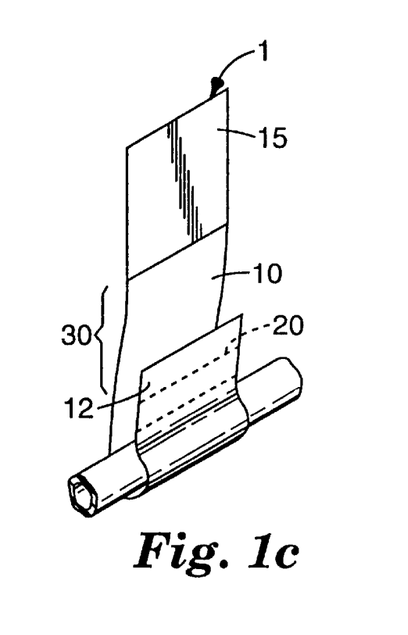

Reference is made to FIGS. 1a–1c wherein like parts have been given like index numbers. Throughout the drawings the various layers of tape, adhesive, or liner material have been exaggerated in thickness for purposes of illustration and clarity. In particular, the adhesive layer is shown in exaggerated thickness. In addition, the size of the various components may be modified, if desired, to accommodate the particular needs of the restraint. FIG. 1a illustrates a cross-section of one restraint of the present invention. This restraint has been drawn to show three main sections ("A", "B" and "C"), although as is clear from the other figures the relationship of these three sections is not necessarily fixed nor are these three section necessarily required (e.g., sections "A" and "C" may be opposite or adjacent to each other or may be combined). Section "A" illustrates one embodiment of the attachment means for securing the restraint to a surface such as a surgical drape or a patient's skin. In this embodiment the attachment means includes tape 15 (comprising adhesive layer 16 and backing 14) and release liner 18. Notably, the release liner covers only part of the adhesive layer. The uncovered portion of the adhesive layer is secured to an elongated strip of flexible material 10 (or "strip"). In manufacture, another portion of release liner (not shown in FIG 1a) is removed from tape 15 prior to securing the tape to the strip. Section "B" illustrates the "loop-section" of the elongated strip of flexible material 10. The loop-section preferably comprises a section which is free of adhesive coatings (i.e., that portion of the strip which contacts the tube or cable when the loop is formed as shown in FIG. 1c is preferably free of adhesive coating). Section "C" illustrates one embodiment of the loop forming means. In this embodiment the loop forming means includes a double-sided adhesive tape (comprising adhesive layers 20 and 26, and backing 24) and release liner 28 secured near the end of the flexible material. In this embodiment, the double-sided adhesive tape has a peel adhesion surface area differential. This peel adhesion surface area differential performs the function of keeping the double-sided adhesive tape adhered to strip 10 at one position (i.e., the peel adhesion surface area differential prevents transfer of the double-sided adhesive tape to another section of the flexible material, e.g., such as might occur when peeling open a loop).

In use, and as illustrated in FIGS. 1b and 1c, release liner 18 is removed thereby exposing adhesive 16. The exposed adhesive portion is positioned against a surface (e.g., a patient's skin or a surgical drape, etc.) and adhered thereto. Next, release liner 28 is removed exposing adhesive strip 20.

The cable or tube is wrapped with the flexible strip as shown in FIG. 1c and adhesive strip 20 is contacted (i.e., secured) against the surface of strip 10 within the adjustment area 30. The adjustment area 30 preferably comprises an area of the flexible strip 10, however one might also secure adhesive strip 20 against the backing surface of tape 15. Preferably, the adjustment area is sized to accommodate a number of different tube sizes. By lengthening the adjustment area (e.g., by lengthening the strip) one can accommodate a larger tube, accommodate more than one tube, or leave enough slack in the loop formed around a tube to allow slip of the tube through the loop. A finger tab 12 is provided to facilitate opening and closing the loop, thereby facilitating "repositionability." The outer surfaces of this tab are preferably free of adhesive.

Figure 1D:
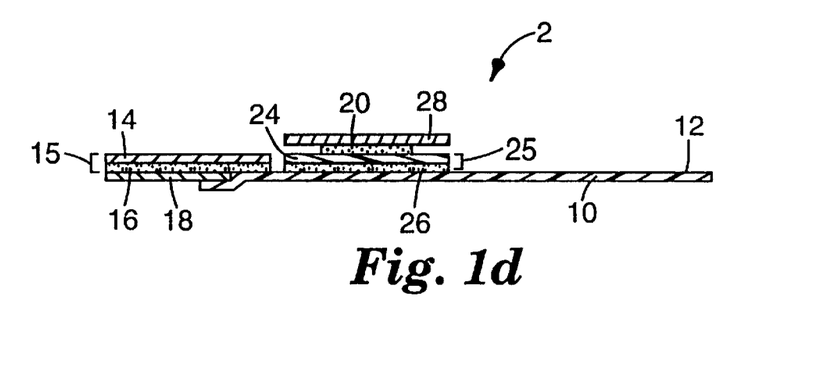
FIGS. 1d, 1e, and 1f illustrate an alternative tube and cable restraint wherein the attachment means and refastenable loop forming means are positioned near the same end of the restraint strap.
Figure 1E:
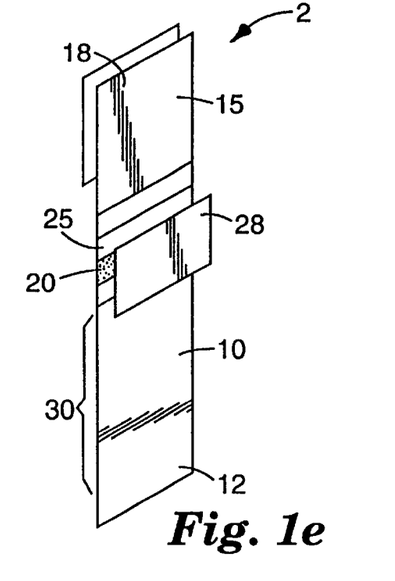
Figure 1F:
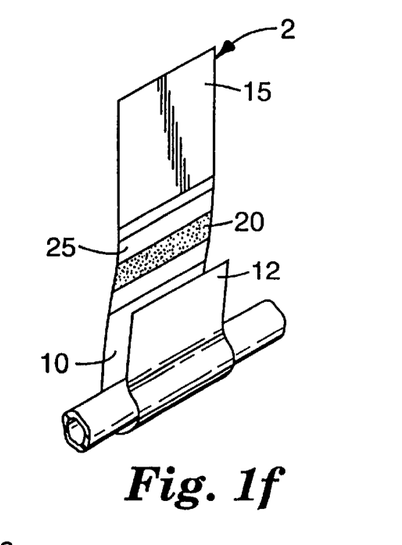

FIGS. 1d, 1e, and 1f illustrate an alternative embodiment of the restraint of the present invention. This embodiment differs from the restraint depicted in FIG. 1a in that the loop forming means is positioned near the same end of the flexible material as the attachment means. In use, and as illustrated in FIGS. 1e and 1f, release liner 18 is removed thereby exposing adhesive 16. The exposed adhesive portion is positioned against a surface (e.g., a patient's skin or a surgical drape, etc.) and adhered thereto. Next, release liner 28 is removed exposing adhesive strip 20. The cable or tube is wrapped with the flexible strip as shown in FIG. 1f and adhesive strip 20 is contacted (i.e., secured) against the surface of strip 10 within the adjustment area 30. The adjustment area 30 comprises an area of the flexible strip 10. Preferably, the adjustment area is sized to accommodate a number of different tube sizes. By lengthening the adjustment area (i.e., lengthening the free end of the flexible material) one can accommodate a larger tube, accommodate more than one tube, or leave enough slack in the loop formed around a tube to allow slip of the tube through the loop. A finger tab 12 (e.g., the free end of the flexible material) is created by the user by simply causing the adhesive strip 20 to contact strip 10 within the adjustment area 30. This leaves a portion of the strip to remain free (i.e., not in contact with the adhesive and not within the loop itself) to facilitate opening and closing the loop, thereby facilitating "repositionability."

Figure 1G:
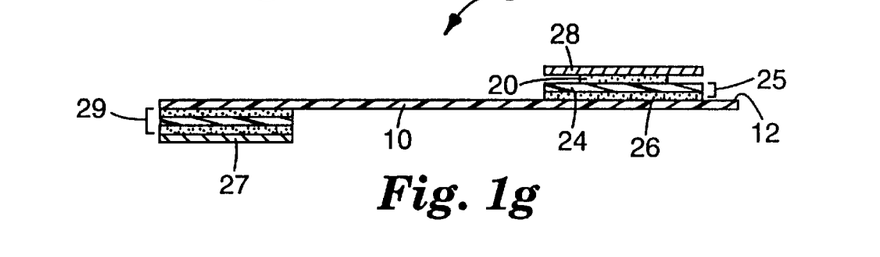
FIG. 1g is a cross section of a tube and cable restraint of the present invention illustrating an alternative attachment means for securing the restraint to a surface.

FIG. 1g illustrates an alternative embodiment of a restraint of the present invention. In particular an alternative attachment means for securing the restraint to a surface such as a drape or skin is illustrated. In this embodiment the attachment means includes a double-stick tape 29 (comprising two adhesive layers and a backing) and a release liner 27. The release liner covers the adhesive layer of the double stick tape which is not in contact with the flexible material 10. In use, not illustrated, release liner 27 is removed thereby exposing a fresh adhesive surface on tape 29. The exposed adhesive portion is positioned against a surface (e.g., a patient's skin or a surgical drape, etc.) and adhered thereto. Next, release liner 28 is removed exposing adhesive strip 20. The cable or tube is wrapped with the flexible strip as shown in FIG. 1c and adhesive strip 20 is contacted (i.e., secured) against the surface of strip 10 within the adjustment area 30.

Figure 1H:
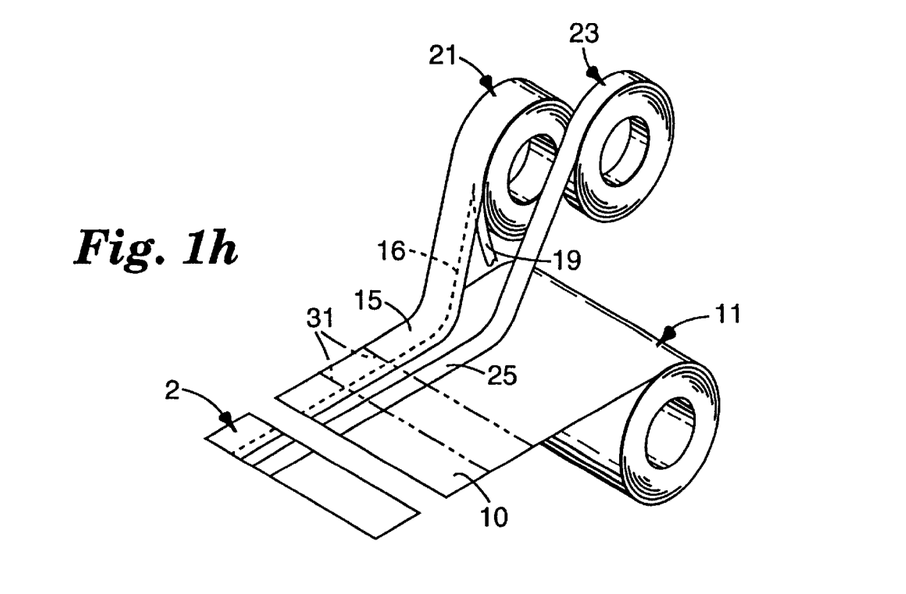
FIG. 1h illustrates a method of making a tube and cable restraint according to the present invention.

FIG. 1h illustrates a presently preferred method of making the restraint of FIG. 1d. Shown in FIG. 1h are three separate rolls ("jumbos") of materials which are first combined, as herein described, and then converted into individual restraints. Roll 11 illustrates a partially unwound large roll of flexible material 10. To the surface of the flexible material 10 is attached, preferably continuously, a strip of tape from roll 21 (comprising tape 15 and liner 18). A portion of liner material 19 is shown being stripped from the tape, exposing a portion of the adhesive layer 16. Another roll of tape 23 (comprising tape 25, adhesive strip 20, and liner 28) is attached, preferably continuously, to the flexible material. To facilitate attachment of the tapes to the flexible material the laminate may be pressed, e.g., between rollers. The position of attachment of tape 23 may be varied as previously discussed (compare FIGS. 1a and 1d). After the tapes are attached to the flexible material the laminate is then converted to width. This may be done using any conventional cutting machine. Individual restraints may thus be made to any desired width. If desired several restraints may be made at one time by laminating additional tapes to a wider sheet of flexible material and slitting the wider sheet into narrower sheets which are then converted.

Figure 2A:
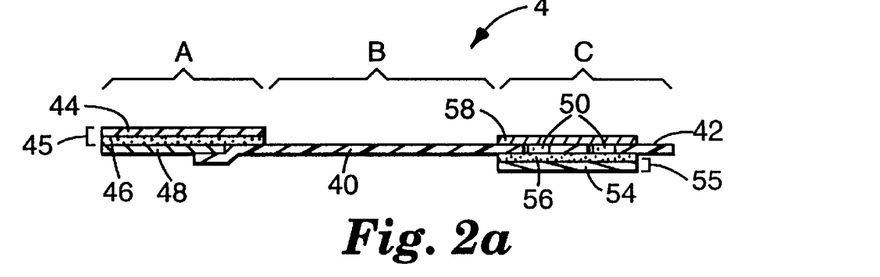
FIGS. 2a, 2b, 2c, and 2d illustrate alternative repositionable loop forming means for holding a tube or cable comprising an apertured restraint strap and a single-sided adhesive tape positioned thereon.

FIG. 2a illustrates a cross-section of an alternative restraint of the present invention. This restraint has been drawn to show three main sections, although as is clear from the other figures and the previous discussion that these three sections are not necessarily required. Section "A" illustrates one embodiment of the attachment means for securing the restraint to a surface such as a drape or skin. In this embodiment the attachment means includes tape 45 (comprising adhesive layer 46 and backing 44) and release liner 48. Notably, the release liner covers only part of the adhesive layer. The uncovered portion of the adhesive layer is secured to the flexible material 40 (or "strip"). In manufacture, another portion of release liner (not shown in FIG. 2a) is removed from tape 45 prior to securing the tape to the strip. Section "B" illustrates the "loop-section" of the elongated strip of flexible material 40. The loop-section preferably comprises a section which is free of adhesive coatings (i.e., that portion of the strip which contacts the tube or cable when the loop is formed as shown in FIG. 2c is preferably free of adhesive coating). Section "C" illustrates an alternative embodiment of the loop forming means. In this embodiment the loop forming means includes adhesive tape 55 (comprising adhesive layer 56 and backing 54) and release liner 58. Adhesive tape 55 is secured near the end of the flexible material and covers one or more apertures 50 through the flexible material. Adhesive layer 56 is exposed wherever an aperture exists. Notably, the number of apertures and the shape of the apertures can be adjusted to provide more or less exposed adhesive, and more or less adhesive "tack". Liner 58 covers these exposed areas of adhesive layer 56 until use of the restraint. If desired, a separate liner may be provided for each exposed spot of adhesive. The separate liners may be removed as additional adhesion is needed.

Figure 2B:
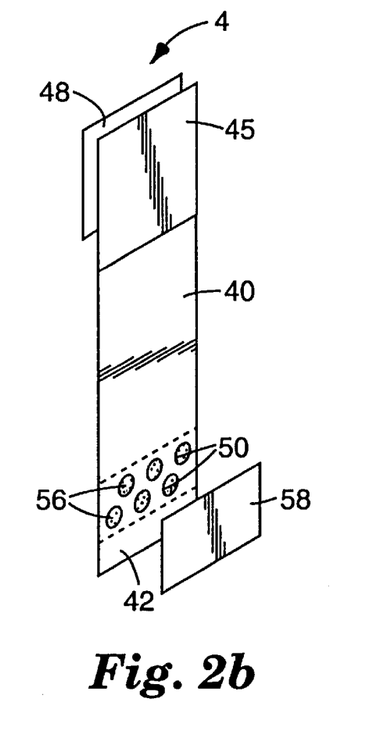
Figure 2C:
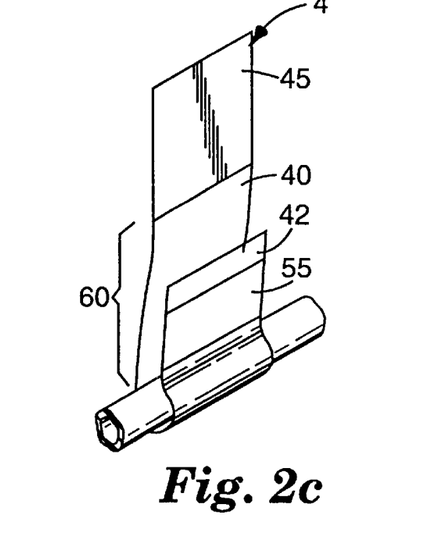

In use, and as illustrated in FIGS. 2b and 2c, release liner 48 is removed thereby exposing adhesive 46. The exposed adhesive portion is positioned against a surface (e.g., a patient's skin or a surgical drape, etc.) and adhered thereto. Next, release liner 58 is removed exposing spot(s) of adhesive 56. The cable or tube is wrapped with the flexible strip as shown in FIG. 2c and adhesive 56 is contacted (i.e., secured) against the surface of strip 40 within the adjustment area 60. The adjustment area 60 comprises an area of the flexible strip 40, however one might also secure adhesive spot(s) 56 against the backing surface of tape 45. Preferably, the adjustment area is sized to accommodate a number of different tube sizes. By lengthening the adjustment area one can accommodate a larger tube, accommodate more than one tube, or leave enough slack in the loop formed around a tube to allow slip of the tube through the loop. A finger tab 42 is provided to facilitate opening and closing the loop, thereby facilitating "repositionability." The outer surfaces of this tab are preferably free of adhesive.

Figure 2D:
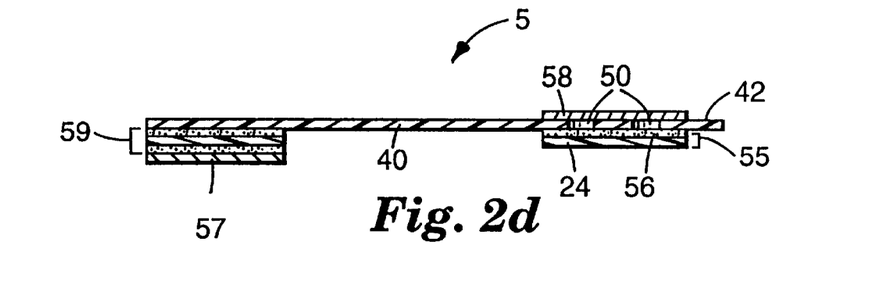

FIG. 2d illustrates an alternative embodiment of the present invention. In this embodiment the attachment means of FIG. 1g is combined with the loop forming means (shown at section "C") of FIG. 2a. In this embodiment the attachment means includes a double stick tape 59 (comprising two adhesive layers and a backing) and a release liner 57. The release liner covers the adhesive layer of the double stick tape which is not in contact with the flexible material 40. In use, not illustrated, release liner 57 is removed thereby exposing a fresh adhesive surface on tape 59. The exposed adhesive portion is positioned against a surface (e.g., a patient's skin or a surgical drape, etc.) and adhered thereto. Next, release liner 58 is removed exposing spot(s) of adhesive 56. The cable or tube is wrapped with the flexible strip and adhesive 56 is contacted (i.e., secured) against the surface of strip 40 within the adjustment area. Preferably, the adjustment area is sized to accommodate a number of different tube sizes. By lengthening the adjustment area one can accommodate a larger tube, accommodate more than one tube, or leave enough slack in the loop formed around a tube to allow slip of the tube through the loop. A finger tab 42 is provided to facilitate opening and closing the loop, thereby facilitating "repositionability." The outer surfaces of this tab are preferably free of adhesive. Alternatively, the loop forming means (comprising apertures 50, tape 55 and liner 58) can be positioned adjacent to the attachment means (comprising tape 59 and liner 57) in a similar manner to the arrangement depicted in FIG. 1d.

Figure 3A:
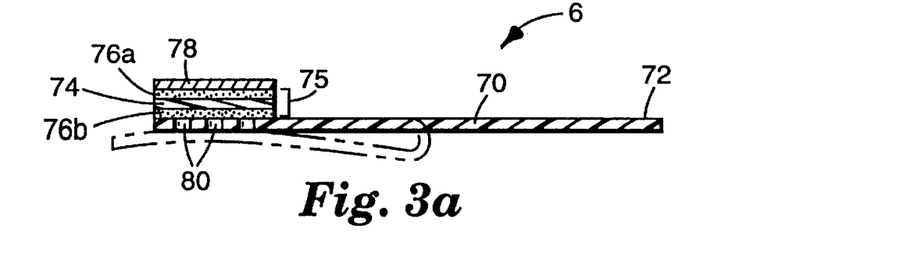
FIG. 3a is a cross section of a tube and cable restraint of the present invention having a combined attachment means and refastenable loop forming means for both securing the restraint to a surface and forming a loop to thereby hold a tube or cable.

FIG. 3a illustrates a cross-section of an alternative restraint of the present invention. This restraint has been drawn to show an combined attachment means and loop forming means. The combined attachment and loop forming means includes a double-stick tape 75 (comprising a backing 74 and two adhesive layers 76a and 76b), a liner 78, and at least one aperture 80. In this embodiment the attachment means includes one side of the double-stick tape 75 (comprising adhesive layer 76a) and release liner 78. The other side of the double-stick tape (comprising adhesive layer 76b) and the apertures 80 form the loop forming means. Adhesive layer 76b is secured to the end of the flexible material and covers one or more apertures 80 through the flexible material. Adhesive layer 76b is exposed wherever an aperture exists. Notably, the number of apertures and the shape of the apertures can be adjusted to provide more or less exposed adhesive, and more or less adhesive "tack". In a preferred embodiment, a portion of flexible material 70 covers these exposed areas of adhesive layer 76b until use of the restraint. That is to say, in a preferred embodiment the restraint is provided in the form of a loop which can be opened to accommodate a tube or cable and reclosed to secure the cable or tube thereto. If desired, a separate liner, not shown, may be provided to cover the exposed spot(s) of adhesive and the restraint may be provided as a strip which can be formed into a loop.

In use, release liner 78 is removed thereby exposing adhesive 76a. The exposed adhesive portion is positioned against a surface (e.g., a patient's skin or a surgical drape, etc.) and adhered thereto. Next, the attached loop is opened (e.g., by peeling flexible material 70 away from the exposed adhesive spots using finger tab 72) and a cable or tube inserted therein. A loop is again formed by wrapping the flexible material 70 around the cable or tube and closing the loop by resecuring the exposed adhesive spots to the flexible material 70 within the adjustment area. A length of flexible material 70 forms the loop (shown in phantom line) and the finger tab 72. The strap preferably comprises a section which is free of adhesive coatings (i.e., that portion of the strap which contacts the tube or cable when the loop is formed as shown in phantom line is free of adhesive coating).

Figure 3B:
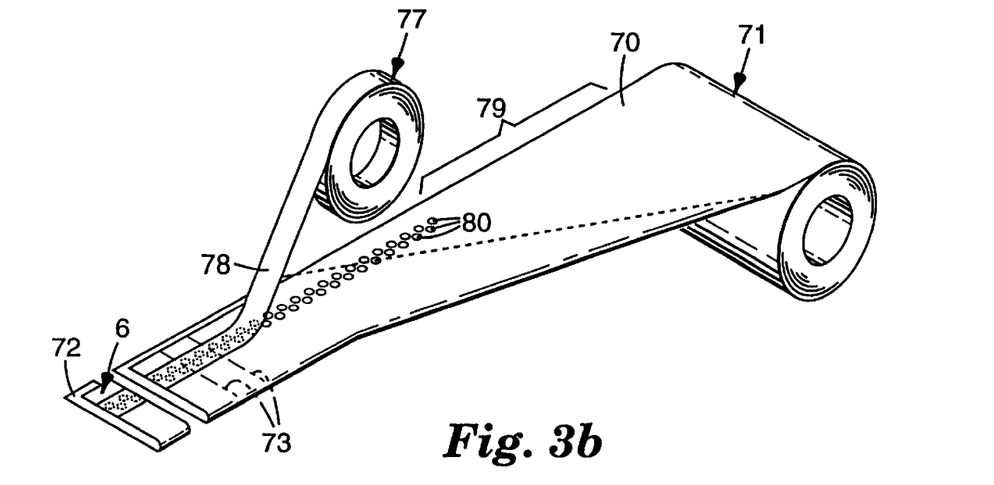
FIG. 3b illustrates a method of making a tube and cable restraint according to the present invention.

FIG. 3b illustrates a presently preferred method of making the restraint of FIG. 3a. Shown in FIG. 3b are two separate rolls ("jumbos") of materials which are first combined, as herein described, and then converted. Roll 71 illustrates a partially unwound large roll of flexible material 70. Near one edge of flexible material 70 are punched a plurality of apertures 80. To the surface of the flexible material 70 is attached, preferably continuously, a strip of double-stick tape from roll 77 (comprising tape 75 and liner 78). The double-stick tape is attached to flexible material 70 covering apertures 80. Flexible material 70 is then folded lengthwise roughly in half to cover the exposed portion of adhesive. Preferably, a portion of flexible material 70 is extended past the edge of the sheet thereby providing a convenient finger tab 72. After the tapes are attached to the flexible material the laminate is then converted to width. This may be done using any conventional cutting machine. Individual restraints may thus be made to any desired width.

Figure 4A:
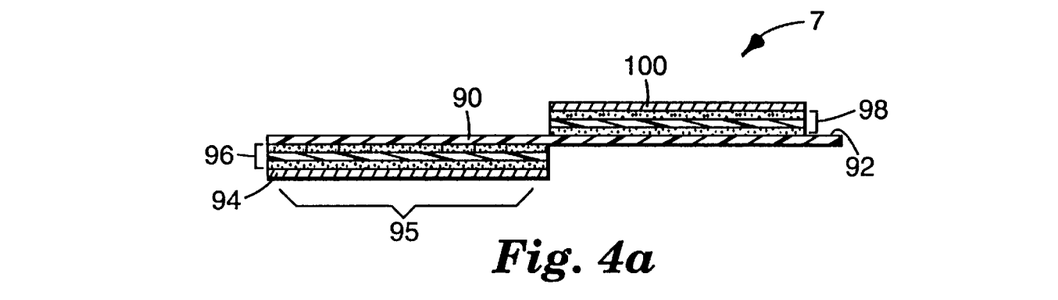
FIGS. 4a and 4b are cross sections of alternative tube and cable restraints of the present invention having an attachment means for securing the restraint to a surface and a refastenable loop forming means for holding a tube or cable.
Figure 4B:
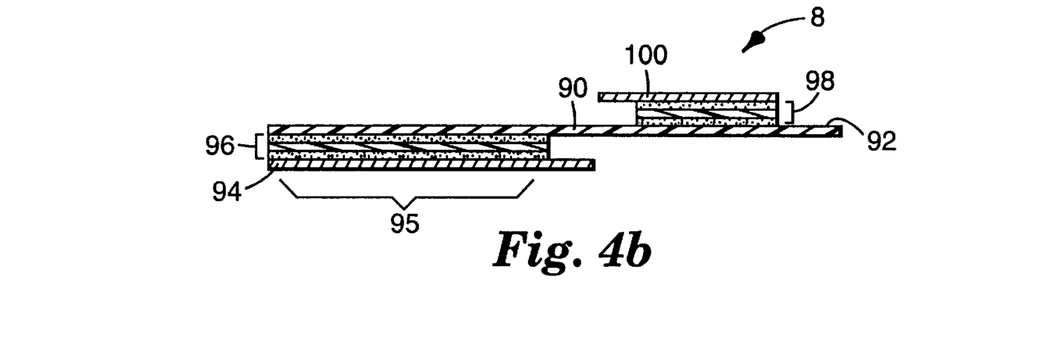

FIGS. 4a and 4b illustrate two alternative embodiments of a restraint of the present invention. In particular an alternative loop forming means (comprising double-stick tape 98 and release liner 100) is illustrated. In this embodiment the attachment means includes a double stick tape 96 (comprising two adhesive layers and a backing) and a release liner 94. The release liner covers the adhesive layer of the double stick tape which is not in contact with the flexible material 90. In use, (not illustrated) release liner 94 is removed thereby exposing a fresh adhesive surface on tape 96. To facilitate the removal of the release liner from the adhesive the release liner may be extended past the edge of the adhesive thereby creating a "tab" of liner which can be easily peeled from the restraint. The exposed adhesive portion is positioned against a surface (e.g., a patient's skin or a surgical drape, etc.) and adhered thereto.

Next, release liner 100 is removed exposing adhesive strip 98. The cable or tube is wrapped with the flexible strip and adhesive strip 98 is contacted (i.e., secured) against the surface of strip 90 within the adjustment area 95. More preferably, and as shown in FIG. 4b, the loop forming means is sized and positioned on the flexible material so as to leave both an inner and an outer portion of the flexible material free of adhesive tape. The inner portion of adhesive free material is wrapped around the cable or tube, thereby not contaminating the cable or tube with adhesive. The outer portion of adhesive free material forms finger tab 92 which can be used to facilitate repositionability of the loop.

FIG. 5 illustrates the "T-Peel" peel force testing mode and the dynamic shear force testing mode for a tube and cable restraint of the present invention.

It is understood that the principles described in this figure apply to other embodiments of the loop forming means and is not considered limiting. To generate a T-Peel force (and measure the T-Peel strength) a suitable tensile testing machine is utilized to pull ends 112 and 113 apart as indicated by arrows A and A'. This causes the loop forming means to peel and separate. Preferably, the loop forming means 125 (comprising in this embodiment adhesive layers 120 and 126 and backing 124) separates between adhesive layer 120 and the adjustment area 130. To generate a dynamic shear force (and measure a dynamic shear strength) a suitable tensile testing machine is utilized to pull ends 114 and 115 of the flexible material 110 as indicated by arrows B and B'. If necessary, the loop-section may be cut to enable the grips of the tensile machine to grab the strip 110 as indicated in FIG. 5.

FIGS. 6a, 6b, and 6c illustrate a surgical drape 140 used for covering a microscope. The drape has a generally tubular construction and comprises a plurality of eyepiece openings 142. To use the eyepiece opening the drape is first ripped along a perforation 144. The microscope eyepiece is threaded through the opening and secured using the restraint 146 of the present invention. One restraint is provided for each opening. The restraint comprises a band-section 148, an attachment means 150 and a band forming means 152. The attachment means 150 may comprise any suitable single-sided tape, double sided tape, or any other suitable mechanical or adhesive attachment means as herein described. For example, the attachment means may comprise a sonic welding of the band to the drape. In one embodiment the band forming means comprises a double-sided tape comprising adhesive layers 154 and 158 and backing 156. Notably, the position of the band forming means is not limited to the particular embodiment disclosed in FIG. 6. For example, the band forming means may be positioned on the flexible strip 148 opposite the attachment means. In use, the user exposes a free surface of adhesive on the band forming means (e.g., by removing a liner material) and wraps the strip around the enclosed object. The free surface of adhesive is contacted against the adjacent layer of strip material, thereby forming a snug band. If desired, the band forming means can be reopened simply by grabbing the finger tab 160 and peeling open. This allows for easy adjustment of the band or for easy removal of the drape after completion of the operation without the need for a sharp knife and without the need to tear the band off. This avoids undesirably stressing the eyepiece and/or possibly damaging it.

Figure 7:
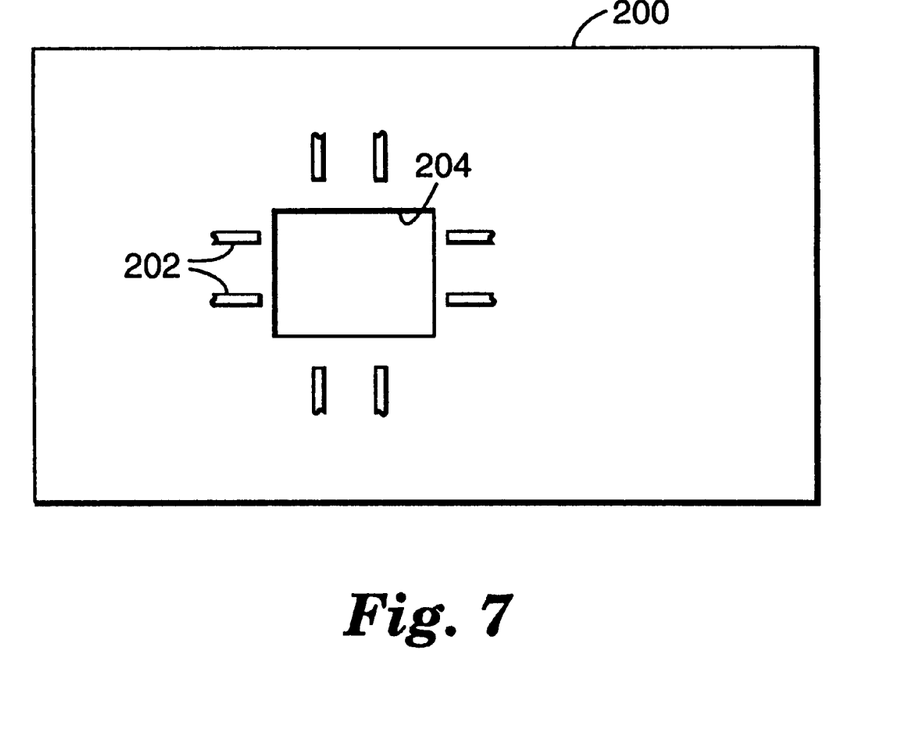
FIG. 7 illustrates a surgical drape of the present invention comprising a plurality of tube and cable restraints attached thereto.

FIG. 7 illustrates a surgical drape 200 of the present invention comprising a plurality of tube and cable restraints 202 attached thereto. The restraints are preferably positioned around an opening or "fenestration" 204 through the drape.

The following examples are offered to aid in the understanding of the present invention and are not to be construed as limiting the scope thereof. Unless otherwise indicated, all parts and percentages are by weight.

EXAMPLES

Example 1

Refastenable Tube and Cable Restraint

Five refastenable tube and cable restraints were produced using a variety of tape components as herein described. To the end of a 3.49 cm wide by 15 cm long rectangular strip of polyethylene film (0.127 mm thick) was attached a 3.49 cm wide by 5 cm long rectangular strip of a single-sided adhesive tape (available from Minnesota Mining Company, St. Paul, Minn., USA) as illustrated in FIG. 1a and as specified in Table 1a. This tape serves as the restraint's "attachment means" for securing the restraint to a surface such as a patient's skin or a surgical drape.

A double-sided adhesive tape (available from Minnesota Mining Company, St. Paul, Minn., USA) was secured to the polyethylene film next to the attachment means (as illustrated in FIG. 1d) forming the loop forming means. The double-sided tape was 3.49 cm wide and 2.5 cm long. On one side of the double-sided tape the adhesive was coated full width (i.e., the surface area of the adhesive coating covered the entire 2.5 cm×3.49 cm area of the tape) with a pressure sensitive adhesive having a thickness of 0.0047 cm. The other side of the double-sided tape was strip coated to a. width of 1.27 cm (i.e., the surface area of the adhesive coating covered the only a 1.27 cm×3.49 cm area of the tape) with a pressure sensitive adhesive having a thickness of 0.0030 m. The fully coated side was placed against the polyethylene film and secured hereto. The narrower exposed adhesive surface was covered with a 2.5 cm×3.49 cm piece of liner material until use.

Table 1a lists the components used for each run and the approximate coating thickness of the adhesive of the attachment means.

TABLE 1A

| Run | Attachment means | Adhesive coating thickness (cm) | Loop forming means |
|---|---|---|---|
| 1 | 3M #1526-SL Clear Tape | 0.0047 | 3M #9920 Tape |
| 2 | 3M #9833-SL White Tape | 0.0047 | 3M #9920 Tape |
| 3 | 3M #9906-SL Tan Tape | 0.0040 | 3M #9920 Tape |
| 4 | 3M #9908-SL White Tape | 0.0038 | 3M #9920 Tape |
| 5 | 3M #1529-SL White Tape | 0.0030 | 3M #9920 Tape |

To test the restraints for peel strength and dynamic shear strength the following operations were performed. A 2 kg rubber coated roller was used to press closed the loop forming means (i.e., adhere the exposed surface of the double-sided adhesive tape to the adjustment area of the flexible material). Peel adhesion force of the loop forming means was measured on an Instron 1122 tensile tester using the "T-Peel" test as illustrated in FIG. 5. The displacement rate of the tensile tester was 30.5 cm/min. Force was measured in grams per 3.49 cm width and converted to N/cm width. In the first test, the opened restraint was closed and initial peel force measured. After the initial peel was measured, closure was repeated and remeasured 6 times. The test was eplicated with 5 restraints. The mean value of initial peel and the mean value or the recycle peel force is reported in Table 1b.

TABLE 1B

| Time (hr) | Peel force (N/cm width) |
|---|---|
| 0 | 0.7765 |
| 1 | 1.1662 |
| 2 | 1.1347 |
| 5 | 1.235 |

Dynamic shear force was measured on an Instron 1122 tensile tester operating at a displacement rate of 30.5 cm/min. Notably, the polyethylene backing failed at a mean force of 10.44 N/cm width and prior to any failure of the loop forming means. This demonstrates that refastenable tube and cable restraints of the present invention peel open easily yet have exceptional dynamic shear strength.

The tensile strength of the polyethylene film was measured by gripping the ends of the film in an INSTRON tensile tester operating at 30.5 cm/min. Notably, the ends of the film were first sandwiched between two pieces of tabbing tape in such a way as to leave only the specified gauge length exposed and to leave the ends of the tape tabs outside the jaw faces. For a 3.49 cm wide sample and a 15 cm gauge length the tensile strength was calculated to be 13.13 N/cm width. Notably, the film broke at only 10.44 N/cm width when the dynamic shear of the loop forming means was being evaluated. The difference in these values is believe to be the result of the resistance to necking imparted by the loop forming means.

Example 2

Dynamic shear force of the attachment means to a typical drape or gown fabric was measured on an Instron 1122 tensile tester operating at 30.5 cm per minute. The various attachment means of the restraints described in Example 1 were adhered to a piece of SONTARA nonwoven fabric (#8818 available from E. I. Du Pont de Nemours Co., Wilmington, Del. 19898). In each case, the polyethylene backing cohesively failed prior to adhesive failure of the attachment means. Thus, refastenable tube and cable restraints of the present invention adhere well to traditional surgical drapes and have exceptional strength.

Example 3

A tube and cable restraint similar to the restraint illustrated in FIG. 2b was prepared. The restraint comprised two pieces of single-sided adhesive tape and a rectangular piece of polyethylene film (35 mm×150 mm). As previously discussed in Example 1, a piece of 1526-SL Clear single-sided adhesive tape was used as the attachment means. Near the attachment means five apertures (6 mm diameter) were punched through the film in two staggered rows (one row having two apertures, the other row having three apertures). A second piece of 1526-SL Clear single-sided tape was placed against the film covering the apertures as illustrated in FIG. 2b. The exposed adhesive of the second piece of adhesive tape was covered prior to use with a liner.

The above tube and cable restraint had peel and shear strengths similar to the restraint of Example 1. In addition, the restraint was easy to use and manufacture.

Various modifications and alterations of this invention will be apparent to those skilled in the art without departing from the scope and spirit of this invention, and it should be understood that this invention is not limited to the illustrative embodiments set forth herein.

What is claimed is:

1. A method of making a refastenable tube and cable restraint comprising the steps of:
    (a) providing a sheet of elongated flexible material having two ends, the first end containing a plurality of apertures
    (b) laminating a combined attachment and loop-forming means containing double-sided tape to the first end of the flexible material, the laminating step yielding a plurality of apertures with exposed adhesive; and
    (c) folding the second end of the flexible material so as to be in contact with exposed adhesive to yield a refastenable tube and cable restraint.

2. The method of claim 1, wherein the total surface area of the apertures does not exceed 70% of the surface area of the double-sided tape.

* * * * *

UNITED STATES PATENT AND TRADEMARK OFFICE
CERTIFICATE OF CORRECTION

PATENT NO.   : 6,187,126 B1  
DATED        : February 13, 2001  
INVENTOR(S)  : Robert J. Rothrum, Robert L. Wheeler and F. Andrew Ubel

It is certified that error appears in the above-identified patent and that said Letters Patent is hereby corrected as shown below:

Column 21,
Line 13, "hereto" should read -- thereto --.

Signed and Sealed this

Fourth Day of June, 2002

Attest:

JAMES E. ROGAN  
*Attesting Officer*        *Director of the United States Patent and Trademark Office*